United States Patent [19]

Hüschelrath et al.

[11] Patent Number: 4,538,108
[45] Date of Patent: Aug. 27, 1985

[54] TESTING ARRANGEMENT FOR FERROMAGNETIC BODIES INCLUDING MAGNETIC FIELD DETECTORS EXTENDING BETWEEN TWO PAIRS OF POLES OF MAGNETIC FIELD GENERATORS SPACED LONGITUDINALLY ALONG THE BODY

[75] Inventors: Gerhard Hüschelrath, Laufach-Frohnhofen; Wilfried Lein, Hanau, both of Fed. Rep. of Germany

[73] Assignee: NUKEM GmbH, Hanau, Fed. Rep. of Germany

[21] Appl. No.: 408,686

[22] Filed: Aug. 16, 1982

[30] Foreign Application Priority Data

Aug. 19, 1981 [DE] Fed. Rep. of Germany ....... 3132808

[51] Int. Cl.³ ...................... G01N 27/82; G01R 33/06
[52] U.S. Cl. ..................................... 324/232; 324/235
[58] Field of Search ............... 324/228, 232, 234, 235, 324/242, 243, 262, 221, 227

[56] References Cited

U.S. PATENT DOCUMENTS

| 2,770,773 | 11/1956 | Cooley | 324/221 |
| 3,710,236 | 1/1973 | Halsey et al. | 324/235 |
| 3,906,357 | 9/1975 | Runshang | 324/227 X |
| 4,087,749 | 5/1978 | McCormack | 324/235 X |
| 4,439,730 | 3/1984 | Kauffman | 324/232 |

FOREIGN PATENT DOCUMENTS

1506642 11/1967 France ................. 324/235

*Primary Examiner*—Gerard R. Strecker
*Attorney, Agent, or Firm*—Cushman, Darby and Cushman

[57] ABSTRACT

An apparatus for non-destructively testing ferromagnetic bodies to determine structural irregularities by means of magnetization of the respective object, comprises detectors for magnetic fields arranged close to the surface of the body, by which detectors any changes of behaviour of the magnetic field caused by structural irregularities can be determined. At least two stationary magnetic fields are arranged one after the other on the body that can be displaced in its longitudinal direction, the center axes of these magnetic fields being inclined toward each other at an angle. This angle is determined by the number of magnetic fields and is equal to the quotient from one hundred and eighty degrees and the number of magnetic fields. In the space between the poles of the magnetic field generators, the magnetic field detectors are stationarily arranged and in rows, each extending over a zone being equal to a body section to be tested, vertically to the shifting direction of the body. The outputs of the magnetic field detectors are connected time-multiplex to an evaluation circuit.

17 Claims, 9 Drawing Figures

TESTING ARRANGEMENT FOR FERROMAGNETIC BODIES INCLUDING MAGNETIC FIELD DETECTORS EXTENDING BETWEEN TWO PAIRS OF POLES OF MAGNETIC FIELD GENERATORS SPACED LONGITUDINALLY ALONG THE BODY

The present invention relates to an apparatus for the non-destructive testing of ferromagnetic bodies for structural flaws by means of magnetization of the respective body, in which the structural flaws cause changes in the magnetic field, which are detected by magnetic field detectors for magnetic fields being arranged at or close to the surface of the body.

It is a known practice when testing ferromagnetic material for cracks, bubbles and holes, to magnetize the work pieces up to saturation. Faults or irregularities in the structure of the material cause the formation of stray flux extending at the places of faults partially outside of the surface of the material. The stray flux is detected by means of magnetic field detectors. The magnetic field detectors enable the localization of structural irregularities. As magnetic field detectors one uses coils, field plates, Hall generators or magnetic powder.

Testing devices for work pieces of complicated shape are equipped with hand magnet yokes, by which magnetic powder is aligned on the surface of the work piece. For work pieces of simple design, e.g. tubes, one uses electromagnets or permanent magnets, generating a magnetic field in the rotating work pieces. Next to the surface of the work piece, approximately in the middle between the two magnetic poles, there is a pair of magnetic field detectors being connected to an evaluating device. Herewith the faults of material extending in direction of the rotational axis can be detected when passing the magnetic field detectors. However, any faults extending diagonally to the rotational axis cannot be detected with such an apparatus. For determining the transverse flaws, additional testing devices must be provided, by which the work pieces are magnetized in longitudinal direction. A belt of magnetic field detectors includes a passage for the work pieces. The work pieces are moved through the belt in direction of the axis. Thereby the magnetic field detectors are detecting the transverse flaws. It is likewise possible to arrange the work pieces non-rotatingly and to make the magnets and detectors rotate around the work pieces.

In non-rotatingly mounted work pieces rotating magnetic fields can be generated in the same way as in electromotors. Herewith one can save the expense and the energy for the rotating of large bulks. Merely the magnetic field detectors must be moved around the work piece synchronously with the rotating field.

When the test objects and the magnetic fields are rotating in relation to each other, eddy currents are induced in the test objects. These eddy currents, by generating magnetic fields of their own, are causing a weakening of the magnetic field internally. Therefore the amplitudes of measured values of faults located inside the bodies are weakened. In order to determine faults inside the bodies to a sufficiently exact extent, the relative rotary motions between the magnetic field and the test piece shall not exceed a few hundred revolutions per minute. Consequently long testing times are required for a complete test of the work pieces. Although the testing time can be shortened by parallelly arranged magnetic field probes, the probe arrangements, however, cannot be made of any length whatsoever. A limit for the length of probe arrangements is at approximately 200 mm. That is to say, a longer test piece section can be magnetized at an unreasonably high expense only, since the energy to be transmitted to the test piece will be rather high. In addition thereto, such probe arrangements must evaluate numerous measuring values at the same time.

For the non-destructive testing of narrowed pipe zones, e.g. of welding seams, one uses devices with stationary pole shoes magnetizing the test zones, and locally arranged magnetic field probes rotating tangentially to the surface. As these probes are moved on a level, the distances to the surface of the test piece will change constantly. Since the measuring sensibility is highly dependent on the distance between the surface of the test piece and the magnetic field probes, with such a device one can only test rather narrow zones with the desired measuring accuracy. As far as welding seams are concerned, these conditions are met. However, it is necessary to exactly place the welding seams in front of the magnetic field probes. This is not entirely possible, even at great expense.

It is the object of the invention to further develop an apparatus of the kind as described at the outset in such a manner that a testing of the ferromagnetic bodies is possible without any rotating magnets or rotating magnetic field probes at a high measuring accuracy and short testing time.

According to the invention this problem is solved in that on the longitudinally movable body at least two stationary magnetic fields are aligned being spaced apart along the body, the center axes of these magnetic fields being inclined against each other at an angle ($\alpha$) being equal to the quotient from one hundred and eighty degrees and the number of the magnetic fields; that in the space between the poles of the magnetic pole means there are positioned rows of stationary magnetic field detectors, each extending over a zone corresponding to a body section to be tested vertically to the advancing of the body; and that the outputs of the magnetic field detectors are connected time-multiplex to an evaluating circuit.

With this testing apparatus comprising stationarily generated magnetic fields and stationary magnetic field probes, the test body is advanced in longitudinal direction. Although there is still a relative movement between the test body and the magnetic field, this relative movement, however, is only presently in axial direction. With rotating test bodies or rotating magnetic poles, relative movements will also appear at places diagonally to the longitudinal axis of the conduit between the surface of the test body and the magnetic field. Consequently, with the above explained apparatus the measuring accuracy will not be influenced by induced eddy currents as no hysteresis takes place. Therefore the speed of the test bodies having a longitudinal extent can be increased in axial direction. This arrangement reduces the testing time. Thus the costs per test body can be essentially reduced with the non-destructive testing. The time-multiplex evaluation of the output signals of the magnetic field probes can be done so quickly that even at a high longitudinal speed of the test bodies, very small surface regions are examined for flaws.

In a preferred embodiment the magnetic field detectors are Hall generators to which control currents can be supplied as pulse sequences, with which a time-multiplex scanning of the Hall generators is being synchronized.

By this pulse operation of the Hall generators the parameters are improved. The result is an increase of the sensibility. Therefore even such Hall generators that normally are used as position sensors only, can now be used for measuring the differences of the magnetic field levels at the different places between two correlated magnet poles. With these Hall generators one can determine fault signals in the dimension of 50 gauss, and that relative to the static base fields generated by the poles, which can thereby be of a strength up to 1 kGauss.

Preferably the ratio of pulse width to pulse interval of the control currents is approximately one to ten. Supplying control currents to the Hall generators in the way of pulses has also the advantage that the probe parameters can be controlled in the pulse intervals. For example, the temperature drift can be sensed. From this correcting values can be obtained, which are set off against the Hall voltages during the admission of the control current in order to increase the measuring accuracy.

In an another embodiment the Hall generators in the rows, with their broadsides are adjusted to the surface of the body.

In still another favorable embodiment the Hall generators in the rows, with their broadsides are arranged vertically to the opposite surface element of the body. With this arrangement one can mount more Hall generators side by side in the respective row. By this means one can detect flaws of very small magnitude.

Preferably at least two layers of Hall generators are arranged one on top of each other in the respective rows. Hereby it is possible to adapt the measuring problem more precisely to the device. Depending on the admissible size of flaw in the body, one can activate e.g. the inner or outer rows of Hall generators for the measuring, or the difference of the two rows in order to measure the vertical field components.

In a further preferred embodiment the outputs of two Hall generators arranged side by side are connected to a difference circuit. Herewith one can measure differences of magnetic fields or field strength gradients.

Another expedient embodiment is characterized thereby that the output signals of the Hall generators can be connected to a compensation amplifier, which via special inputs can be supplied with compensation values for signal portions in the Hall voltages of the Hall generators reducing the measuring accuracy. By this arrangement one can remove the disturbing static components included in the Hall voltages before the signals are reprocessed. Such disturbing components do appear since depending on the angle position of the respective Hall generator relative to the axis of the magnetic field extending through the center of the longitudinal body, disturbing signal components of different magnitudes will arise that can be removed with the above explained arrangement. Further undesired signal components will appear if the body is moved out of its centric test position opposite of the magnetic fields. This displacement can be measured. Compensation values corresponding to the respective displacement will remove the measuring error caused by such displacement.

Preferably a detecting filter is connected after the compensation amplifier. Such detecting filters are also known by the name of matched filters. These are filters used for the prevention of interfering signals in adaptation to the special form of useful signals. Herewith one can obtain an additional improvement of the signal-to-noise ratio.

In still another preferred embodiment it is provided that the evaluation circuit has a processor connected to a bus, which processor is also connected to a trigger circuit, with the output signals of which the control currents of a constant current generator feeding the Hall generators can be synchronized, and that connected to the bus are the matched filter and the control inputs of a multiplexer arranged between the outputs of the Hall generator and the compensation amplifier, as well as the inputs of registers, of which the outputs are connected to the the inputs of the compensation amplifier. By this arrangement the Hall voltages can be sensed, compensated and assigned accurately to a specific incremental region the surface of the test body. Thus the localization of the fault is much easier.

In still another expedient embodiment the body, in axial direction, is charged by an additional magnetic field, where the longitudinal axes of the Hall generators are oriented in the rows at a torsional angle relative to the center axes. This arrangement enables the determination of flaws extending diagonally to the longitudinal axis of the body.

In a preferred embodiment the body, in axial direction, is charged by an additional magnetic field, while at least two rows of Hall generators are arranged side by side and with each other form an angle of 90°, and where the outputs of the Hall generators in the rows each time are connected with each other in a difference circuit. With this arrangement one can sense the direction of the magnetic field and thus the direction of the imperfection.

Preferably the additional magnetic field is a magnetic alternating field having a low frequency.

Further details, characteristics and advantages of the invention will result from the following description of the diagrammatically shown examples of embodiment.

FIG. 2 shows the arrangement of FIG. 1 in front elevation, FIG. 3 shows details of the rows of magnetic field detectors presented in FIG. 1, in front view, FIG. 4 shows an embodiment of a different arrangement of a row of the magnetic field detectors in front elevation.

FIG. 5 is a sectional view of the row shown in FIG. 2,

FIG. 6 is a sectional view of the row shown in FIG. 3,

FIG. 8 shows diagrams of Hall voltages generated by the Hall generators in a row depending on the position in the row.

Figure 1:
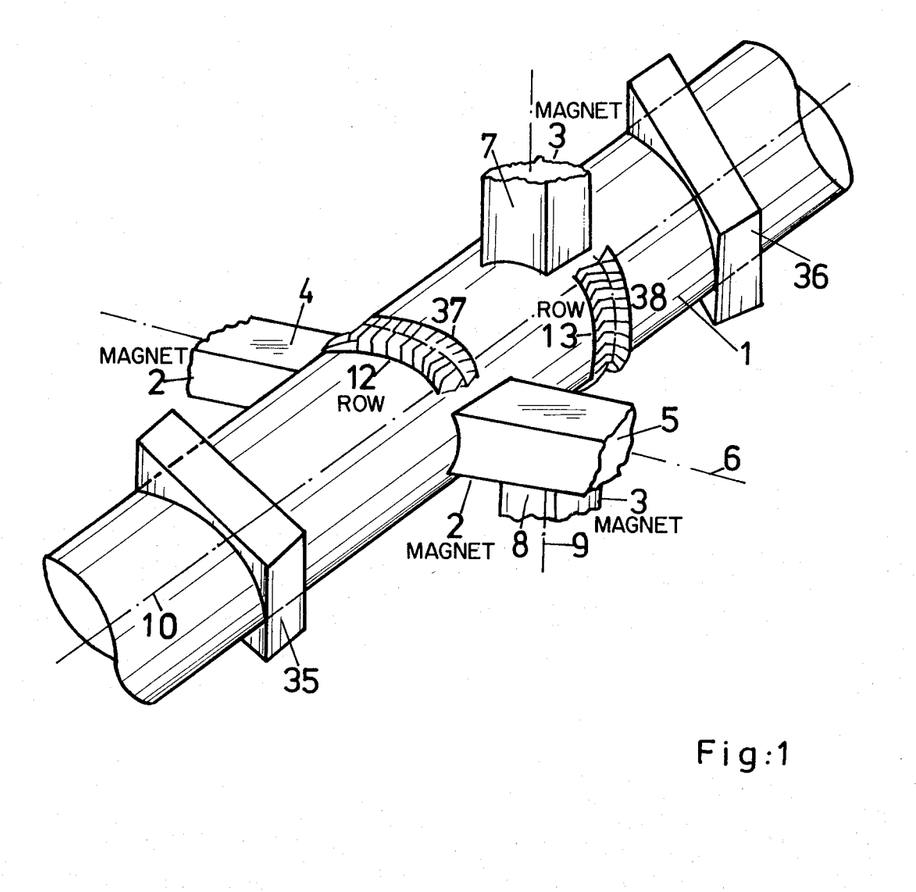
FIG. 1 is a perspective view of an apparatus for the non-destructive testing of ferromagnetic bodies.

An apparatus for the non-destructive testing of ferromagnetic pipes 1, of which one is being shown in FIGS. 1 and 2, comprises a magnetizing system of two pairs of magnets 2, 3 being spaced apart in longitudinal direction of the pipe 1. The magnet pair 2 comprises a first magnet pole shoe 4, the end of which facing the pipe 1 being e.g. a magnetic north pole, and a second magnet pole shoe 5, which at its end facing the pipe 1 has a magnet pole being opposite to that one of the first pole shoe 4. The magnet pole shoes 4, 5 are arranged along the same center axis 6. The magnet pair 3 is likewise composed of two magnet pole shoes 7, 8 where the pole shoe 7 has a magnetic north pole on its front surface facing the pipe 1, and the pole shoe 8 has a magnetic south pole on its front surface adjacent to the pipe 1. The magnet pole shoes 7, 8, too, are arranged along a common center axis 9. While the magnet pairs 2 and 3 are stationarily mounted, the pipe 1 during the testing operation, in direction of its longitudinal axis 10, is moved through between the magnet pole shoes 4, 5, 7 and 8. By the magnet pole shoes 4, 5, 7 and 8 two magnetic fields are pointed at the pipe 1. Each of the center axes of these magnetic fields is coinciding with the center axes 6 and 9 of the magnet pole shoes 4, 5 or, resp. 7, 8. The center axes 6 and 9 are inclined at an angle toward each other, which angle is equalling the quotient from one hundred and eighty degrees and the number of the magnetic fields aimed at the pipe 1. As two magnetic fields are pointed at the pipe 1, the angle α is ninety degrees. The field lines of the magnetic fields inside of the pipe are extending mainly in the walls of the conduit. The magnetic fields are designed so strongly that the pipe walls are magnetically saturated.

By cracks, flaws and holes in the pipe walls the magnetic resistance is heavily increased. A portion of the magnetic field will not close over the cracks, flaws or holes but rather over the air gap outside of the outer or, resp. inner surface of the conduit. This portion of the magnetic field is sensed by magnetic field detectors. The measurement of such a field extending outside of the surface of the pipe will thus indicate a flaw in material or, respectively, a structural irregularity in the walls of the pipe 1.

Between the pole shoes 4, 5 or, resp. 7, 8 directing the magnetic fields toward the pipe 1 there are arranged rows 12 or, resp. 13 of magnetic field detectors along the surface of the pipe 1. The rows 12, 13 are positioned at a small distance from the surface of the pipe 1. In FIGS. 1 and 2 the rows 12 and 13 are arranged close to the outer walls of the pipe 1. One can also arrange rows of magnetic field detectors in the inside of the pipe 1, extending along the inner surface thereof.

The rows 12, 13 are covering a testing zone in the pipe 1 that extends in axial direction 10 and has a width corresponding to the length of the respective row 12 or, resp. 13. The rows 12, 13, like the magnet pairs 2, 3, are stationarily arranged. The two rows 12 and the two rows 13 are each covering two zones on the surface of the conduit 1, each of the zones including an angle β resulting from one hundred and eighty degrees divided by the number of the magnet poles. Each individual row 12, 13 includes at least this angle of 45°. The rows 12, 13 can also be of greater length, so that an angle β will result being greater than 45°. With the size of rows 12 and 13 as shown in FIGS. 1 and 2 one can test the pipe 1 over its entire extent.

In case one needs a testing apparatus for testing the pipe 1 not over its entire bulk but rather over a portion thereof only, which e.g. is equalling the width of a welding seam, then a row of magnetic field detectors can be provided having only the width of the desired portion of the bulk. Hereby the use of one magnet pair only can suffice. The testing apparatus shown in the FIGS. 1 and 2 can be operated by switching in such a manner that not only the entire bulk but also a portion thereof only can be tested. This will be explained in more detail in the following.

In the rows 12, 13 Hall generators are provided as magnetic field detectors, to which pulse sequences are supplied as control currents. The outputs of the Hall generators in time-multiplex are connected to an evaluation circuit, which will be described still in the following. The time-multiplex scanning of the Hall generators is synchronized with the pulse sequences of the control currents. For Hall generators one can use such of the type KSY 10 of the firm Siemens.

In the rows 12, 13 Hall generators 14, 15 can be arranged in different alignment to the surface of the pipe 1. In FIG. 4 and FIG. 6 Hall generators 14 are shown, of which the broadsides 16 are adjusted to the surface of the pipe 1. There are two layers 17, 18 of Hall generators one on top of the other. Which layer 17, 18 of Hall generators 14 will be used for the detecting of faults is depending on the kind of test. The highest sensibility for the detection of faults will result from the difference circuiting of adjacent Hall generators in the layers 17 and 18.

In the embodiment as shown in FIGS. 3 and 5 the Hall generators 15 with their broadsides 19 are arranged vertically to the opposite surface element of the pipe 1. The Hall generators 15 are mounted in two layers 20, 21 one on top each other.

The use of the respective layer 20, 21 for fault testing (also for the arrangement as shown in FIG. 4) is depending on the selection criteria of the faults. The embodiment according to FIG. 3 permits a tight packing of Hall generators 15 side by side. By this arrangement faults in the structure of the conduit 1 can be better localized.

Figure 7:
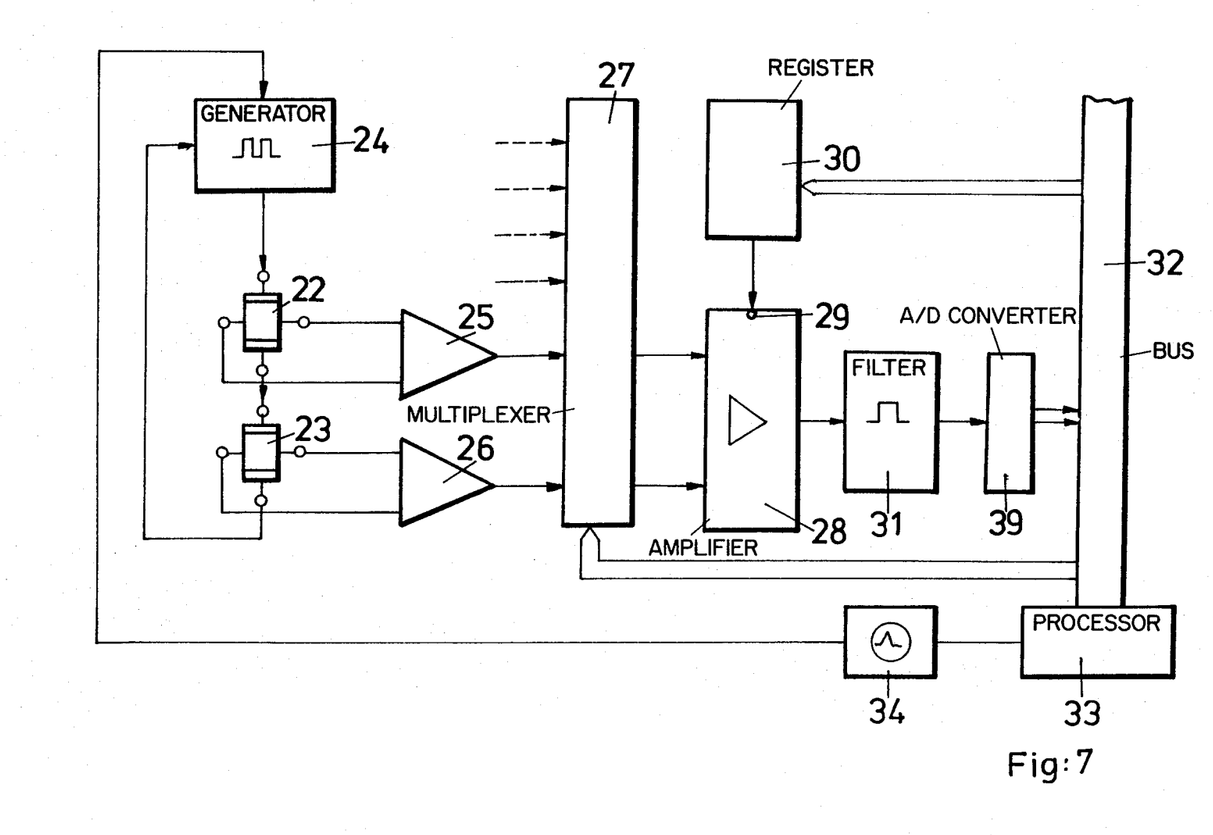
FIG. 7 is a block diagram of an evaluation circuitry connected to magnetic field detectors.

FIG. 7 shows two Hall generators 22, 23 together with their connection electrodes. The rows 12, 13 are composed of Hall generators according to the kind of arrangement 14, 15. The manner of connection of all Hall generators 14, 15 forming adjacent pairs in one of the layers 17, 18 or 20, 21 corresponds to that one of the two Hall generators 22, 23.

The feeding electrodes for the control current in the Hall generators 22, 23 are series-connected. A constant current generator 24 feeds the supply electrodes for the control current. The electrodes for taking up the Hall voltage are each connected to an input of an amplifier 25, 26 as far as the Hall generators 22, 23 are concerned.

The constant current generator 24 produces a pulse sequence at a pulse interval-to-pulse width ratio of 1 to 10. By supplying pulses to the Hall generators 22, 23 the thermal stress is reduced. Therefore higher control current amplitudes can be applied. As the Hall voltage is proportional to the control currents, even small magnetic fields will yield sufficiently high Hall voltages. An increase of the parameters of the Hall generators 22, 23 takes place. Therefore, as Hall generators 22, 23 one can use inexpensive sensors, e.g. the types KSY 10, which normally are used for the scanning of position of magnets. The pulse-wise charging of the Hall generators 22, 23 with control currents does likewise permit the monitoring of selected values in the pulse intervals. In this manner it is possible to determine in the pulse intervals the temperature-conditional zero constancy of the Hall generators 22, 23 and to fix correcting values in accordance with the temperature values, with which the measured values for preventing the influence of temperature changes are corrected.

The outputs of the amplifiers 25, 26 are connected to inputs of a multiplexer 27, to which there are likewise connected the amplifiers fed by the other Hall generators 14 or, resp. 15 (not shown in further detail). The outputs of the multiplexer 27 to which the analog signals are fed by the amplifiers 25, 26 or the other amplifiers (not shown), are connected to two inputs of a compensation amplifier 28. The compensation amplifier 28 has inputs 29 for the admission of compensation values. For a compensation amplifier 28 one can use e.g. one or several operation amplifiers of the type Harris 2525. The inputs 29 are fed from the outputs of a register 30, in which the digital compensation values are intermediately stored during the time of compensation of the signals in the compensation amplifier 28. The register 30 is further equipped with a digital-analog converter, (not shown), e.g. one of the unit made by Messrs. Datel of the type DAC 12 HA. The output of this converter is feeding the inputs. By the compensation, the signals generated by the Hall generators 22, 23 are freed from interfering static signal portions. Furthermore the compensation amplifier 28, in a corresponding connection will produce the difference of the signals of the Hall generators. The result of this difference formation is a signal corresponding to the gradient of the magnetic field strength at the place of the Hall generators 22, 23, which signal being reduced for the local d.c. field portion reflected by the reference signal. The difference of the signals is further increased and supplied to a tracing filter (matched filter) 31 being connected to the compensation amplifier 28. The tracking filter 31 has a characteristic being adapted to the form of the useful signals of the Hall generators 22, 23, by which the interfering signals are suppressed even more. With such a tracing filter the ratio of signal-to-noise can be improved for a factor between 10 and 20. An analog-digital converting unit 39 is connected to the tracking filter 31. With the converting unit 39 digital signals are generated, corresponding to the Hall voltage differences of the generators 22, 23 less the local d.c. field portion. The digital signals have several binary or binary coded places. The outputs of the converter unit are connected to a bus 32. Likewise connected to the bus 32 are the inputs of the register 30. Furthermore the control inputs of the multiplexer 27 are connected to the bus 32. Preferably the bus 32 has separate addressing and data lines.

The bus 32 is furthermore connected to a processor 33, which controls the generation of addresses and the data transfer on the bus 32. The processor 33 is connected to a trigger arrangement 34, which is connected to the constant current generator 24. The trigger arrangement 34 synchronizes the control current pulses of the constant current generator according to the processor 33.

The Hall generators 14, 15 in the rows 12, 13, in that sequence as defined by their position in the rows 12, 13, one after the other are connected to the compensation amplifier 28 via the multiplexer 27 controlled by the processor 33. By this electronic scanning of the Hall generators 14, 15 the rotation of a magnetic field probe is electronically simulated. The successive scanning of the Hall generators 14, 15 can be done rather quickly by using non-contacting control elements. Thereby a "rotation speed" is simulated, being essentially higher than the speeds of rotatable magnetic field probes that can be profitably reached with mechanic means.

The selection and the sequence of the Hall generators 14, 15 can be changed at option by means of a corresponding addressing of the multiplexer 27. Thereby the device shown in FIG. 7 in the block diagram can be adapted to different testing conditions. If e.g. only small pipe areas shall be tested, the scanning can be restricted to the Hall generators 14, 15 facing this section of the conduit. In addition thereto it is possible to scan critical pipe sections more often than other areas thereof by a quicker addressing of the multiplexer. The apparatus can thus be used more universally than the initially described testing devices.

The rows 12, 13 of the magnetic field probes can be likewise adapted to oblong bodies not having a round cross section, while the initially explained testing devices with rotating magnets or magnetic field probes are only suitable for bodies with round cross sections.

If the apparatus shall be used for the testing of small pipe sections only, the row 12 or, resp. 13 of magnetic field probes can be adapted each time to the extent of these areas. By selecting adequate distances relative to the test object, the the arrangement of the probes in their respective row 12, 13 can be easily adapted to the surface contour. By adapting the rows 12, 13 to the surface contour one can save the high expenses for a very exact guiding of the test body. The respective segment can also be selected so small that its size will correspond to that of hand yoke magnets. It can then be operated together with hand yoke magnets. In this manner work pieces of any shape and size whatsoever can be tested segment by segment.

Due to the different distances of the Hall generators 14 or, resp. 15 arranged in the rows 12, 13 to the magnet pole shoes 4, 5 or, resp. 7, 8, the generated Hall voltages likewise are different. FIG. 8 shows the curves of the Hall voltages $U_H$ of Hall generators arranged in a row, being contingent on the angle position $\alpha$. Thereby the angle 0° has been coordinated with the middle between two magnet poles 4, 5 or, resp. 7, 8. At the places marked with 45° there are the upper edges of the magnet pole shoes 4, 5 or, resp. 7, 8. In the vicinity of these magnet pole shoes the Hall voltages $U_H$ are higher than at the 0° place. The Hall voltages $U_H$ present a parabolic curve. The curve marked with I is present if the longitudinal axis 10 of the pipe 1 is extending centrically to the longitudinal axes of the magnet pairs 4, 5; 7,8. For pipes displaced off-center, the Hall voltage $U_H$ shows a different curve. The curve II will result from a position where the conduit 1 with its longitudinal axis 10 is shifted to the right from its position shown in FIGS. 1 and 2. The curve III of the Hall voltage $U_H$ will appear at a shifting of the pipe 1 into a position located to the left of the shown position.

This influence of position on the Hall voltages $U_H$ of the Hall generators must be removed in order to obtain a high measuring accuracy. The processor ee comprises a storage unit (not shown), containing the correction values for the different positions of the Hall generators 14 or, resp. 15. The correction values refer to both the centric arrangement of the pipe 1 and to off-center positions. The position of the pipe 1 is determined e.g. prior to starting the testing for structural faults by the reception of a Hall voltage curve, as it is shown in FIG. 8. This Hall voltage curve supplies a compensation value for the position of the respective Hall generator 14 or, resp. 15, which will then be stored. Prior to scanning of the respective Hall generator, the matching compensation value is fed to the register 30. The Hall voltages supplied to the compensation amplifier 28 are then corrected with the compensation values from the register 30.

The successive scanning of the Hall generators 14 or, resp. 15 with non-contacting control elements enables a sufficiently high fault discrimination even at high speeds of the pipe 1 in longitudinal direction 10. In case shifting speeds are desired where the series scanning with quick switching circuits does not suffice, then the Hall generators 14 or, resp. 15 can be scanned at the same time. To this effect one has merely to increase the expense for switching equipment. For example, one needs several multiplexers and compensation amplifiers together with registers for the compensation values.

The Hall generators 14 or, resp. 15 are preferably mounted in a supporting block of a non-iron metal, where the Hall generators are arranged so close to each other than no dead zone can develop between them.

Favorable distances of the Hall generators 14 or, resp. 15 from the surface of the pipe 1 are found within the range of 1 mm to 1,5 mm.

When testing a ferromagnetic pipe of a diameter of 65 mm and a wall thickness of 5 mm with an apparatus provided with Hall generators being arranged in such a manner, it resulted the signal-to-noise ratio indicated in the following table, contingent on the depth and position of the faults.

| Fault Depth | Fault Position | Signal-to-Noise Ratio |
| --- | --- | --- |
| 5% | inside | 6 dB |
| 10% | inside | 10 dB |
| 5% | outside | 8 dB |
| 10% | outside | 17 dB |

These results were obtained independently of the angle position of the Hall generators. The measured values have been taken at the output of the tracing filter 31.

With the above described apparatus one cannot detect flaws extending diagonally to the longitudinal direction of the pipe 1. As flaws always have a spatial dimension and the Hall generators have small dimensions, such faults can still be detected via their stray flux. However, it is possible to develop the above described apparatus in such a manner that one can also detect flaws with a purely transverse extension with a high degree of accuracy. To this effect the conduit will be magnetized in its longitudinal direction, too. This longitudinal magnetizing can be caused by two annular magnet pole shoes 35, 36 belonging to a magnet system, each being clamped vertically around the outer surface of the pipe 1. The magnet pole shoes 35, 36 are provided at a distance to each other on different places of the surface of the pipe. The generation of a longitudinal magnetization of the magnet pole shoes 35, 36 will not impede the advancing of the pipe in longitudinal direction. In order to detect the gradients of the magnetic fields extending in longitudinal and diagonal directions in case of flaws in the conduit 1, the Hall generators 14 or, resp. 15 with their plates are rotatably arranged in the rows 12, 13. Hereby the longitudinal axes of these plates (not shown in any further detail) are inclined toward the center axes 6, 9 of the magnetic fields. The extent of the inclination of the little plates relative to these center axes 6, 9 or, resp. the longitudinal axis 10 is contingent on the field strengths in longitudinal and diagonal directions of the pipe 1. The pole shoes 35, 36 are preferably part of an electromagnet, by which a magnetic a.c. field of low frequency is generated. Herewith a magnetic field is produced in the pipe 1, of which the field strength vectors are periodically oscillating around a main axis. The resulting field strength is set so high that there will be an optimum indication of faults.

Adjacent to each row 12, 13 of Hall generators 14 or, resp. 15, as seen in axial direction of the pipe 1, one can also arrange a second row 37, 38 of Hall generators. Thereby the longitudinal axes of the little plates of the Hall generators in the adjacent rows 12, 37 or, resp. 13, 38 are extending vertically into each other. With the Hall generators in the different rows 12, 13, 37, 38 the field strength gradients can be detected that extend perpendicularly to each other. From the two gradients one can find out the direction of the extension of a flaw.

Figure 9:
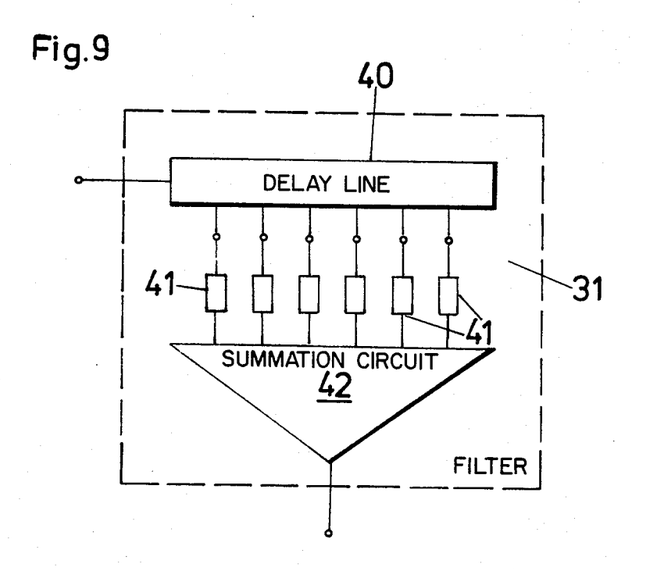
FIG. 9 is a block diagram of a detecting filter.

FIG. 9 shows the construction of the tracking filter 31. After the input of the tracing filter a delay line 40 with tappings is connected, (not described in any further detail). To the tappings resistors 41 are connected, being of different weight in adaptation to the form of the input signals. Connected to the resistors 41 is a summation circuit 42 which generates the output signal. As a delay line for such a tracing filter one can use e.g. the type Data Delay 2214-2000 G.

We claim:

1. An apparatus for non-destructively testing for structural irregularities in a ferromagnetic body having a longitudinal extent comprising:

first magnetic pole means, including at least two magnetic poles, for generating a first stationary magnetic field having a first central linear axis passing through said two magnetic poles and radially through said body;

second magnetic pole means, including at least two magnetic poles spaced apart along said body from said first magnetic pole means, for generating a second stationary magnetic field having a second central linear axis passing through said two magnetic poles and radially through said ferromagnetic body, said first and second central axes being inclined with respect to one another at an angle α which is substantially equal to 180°/N, where N is the total number of magnetic fields generated by said apparatus;

means for longitudinally displacing said body with respect to the poles of said first and second magnetic pole means;

a plurality of rows of stationary Hall generators, each row extending either in a space between the magnetic poles of the first magnetic pole means or between the magnetic poles of the second magnetic pole means, for detecting a magnetic field over a zone corresponding to a section of said body perpendicular to the displacing direction of said body, said Hall generators providing detector signals indicative of the fields sensed thereby;

means for time multiplexing said detector signals to form a time multiplexed signal;

a pulse sequence control circuit for driving said Hall generators and to which said time multiplexed signal can be synchronized;

means for generating compensation values for various signal levels of said Hall generators as a function of the position of the Hall generator whose output is being compensated;

a compensation amplifier for compensating said time multiplexed signal with said compensation values; and means for analyzing said compensated time multiplexed signal.

2. Apparatus according to claim 1 wherein the rows of Hall generators are arranged symmetrically with respect to said first and second central axes and are of sufficient size and positioned so as to extend over a zone including an angle $\beta$ equal to or greater than $180°/M$, where M is the number of magnetic pole means of said apparatus.

3. Apparatus according to claim 1 wherein said pulse sequence control current comprises a control current wherein the ratio of pulse width to pulse interval is approximately 1:10.

4. Apparatus according to claim 1 wherein each Hall generators includes a broadside and wherein the broadsides of said generators are aligned to the surface of said body.

5. Apparatus according to claim 3 wherein each Hall generators includes a broadside and wherein the broadsides of said generators are aligned to the surface of said body.

6. Apparatus according to claim 1 wherein each Hall generators includes a broadside and wherein the broadsides of said Hall generators are aligned perpendicularly to an opposite surface section of said body.

7. Apparatus according to claim 3 wherein each Hall genreators includes a broadside and wherein the broadsides of said Hall generators are aligned perpendicularly to an opposite surface section of said body.

8. Apparatus according to claim 6, wherein in respective rows there are arranged two layers of Hall generators one layer being on top of the other.

9. Apparatus according to claim 8, wherein in respective rows there are arranged two layers of Hall generators one layer being on top of the other.

10. Apparatus according to claim 8 further including means, coupled to outputs of two Hall generators, for differentiating the signals therefrom.

11. An apparatus according to claim 1 wherein said analyzing means further comprises a tracing filter coupled to said compensation amplifier.

12. An apparatus according to claim 1 further comprising a block fabricated from a non-iron metal for receiving a row of Hall generators.

13. An apparatus according to claim 1 wherein said Hall generators are positioned 1 mm–1.5 mm from the surface of said body.

14. An apparatus according to claim 1 further including means for generating an additional magnetic field along the axial direction of said body and wherein the Hall generators of a row are arranged non-uniformly relative to the center axis of their corresponding magnetic poles.

15. An apparatus according to claim 1 further including means for generating an additional magnetic field along the axial direction of said body and wherein at least two rows of Hall generators are arranged side-by-side, wherein the longitudinal axis of the little plates of the Hall generators in adjacent rows define with each other an angle of substantially 90° and further including means for differentiating the outputs of adjacent Hall generators.

16. An apparatus according to claim 14 wherein said additional magnetic field generating means comprises two magnetic pole shoes, each pole shoe being clamped around the body and being mounted in the longitudinal direction of said body spaced from each other, the rows of Hall generators being arranged between the magnetic pole shoes.

17. An apparatus according to claim 12 wherein said additional magnetic field comprises a low frequency AC magnetic field.

* * * * *